(12) United States Patent
Reicher et al.

(10) Patent No.: US 10,832,808 B2
(45) Date of Patent: Nov. 10, 2020

(54) AUTOMATED SELECTION, ARRANGEMENT, AND PROCESSING OF KEY IMAGES

(71) Applicant: INTERNATIONAL BUSINESS MACHINES CORPORATION, Armonk, NY (US)

(72) Inventors: Murray A. Reicher, Rancho Santa Fe, CA (US); James G. Thompson, Escondido, CA (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 34 days.

(21) Appl. No.: 15/840,689

(22) Filed: Dec. 13, 2017

(65) Prior Publication Data

US 2019/0180863 A1 Jun. 13, 2019

(51) Int. Cl.
| | | |
|---|---|---|
| *G16H 30/40* | (2018.01) | |
| *G16H 30/20* | (2018.01) | |
| *G06K 9/66* | (2006.01) | |

(52) U.S. Cl.
CPC ............ *G16H 30/40* (2018.01); *G06K 9/66* (2013.01); *G16H 30/20* (2018.01)

(58) Field of Classification Search
CPC . G06T 2207/10116; G06T 2207/10132; G06T 2207/30004; G06T 2207/30068; G06T 2207/30096; G06T 7/0012; G06K 9/66; G16H 40/63; G16H 50/20; G16H 30/20; G16H 50/70; G16H 30/40
See application file for complete search history.

(56) References Cited

U.S. PATENT DOCUMENTS

| | | | |
|---|---|---|---|
| 6,090,044 A | 7/2000 | Bishop et al. | |
| 6,574,304 B1 | 6/2003 | Hsieh et al. | |
| 6,687,329 B1* | 2/2004 | Hsieh ................ | A61B 6/032 378/62 |
| 6,819,790 B2 | 11/2004 | Suzuki et al. | |
| 6,836,558 B2 | 12/2004 | Doi et al. | |

(Continued)

OTHER PUBLICATIONS

Filed Dec. 13, 2017, U.S. Appl. No. 15/840,689.

(Continued)

*Primary Examiner* — Jingge Wu
(74) *Attorney, Agent, or Firm* — Michael Best & Friedrich LLP (57) ABSTRACT

A method and system is provided for automatically determining a key image for display to a user as part of analyzing an image study generated as part of a medical imaging procedure. The system includes a memory storing a plurality of image studies, a display device for displaying images and an electronic processor interacting with the memory and the display device. The electronic processor is configured to determine a first key image within a plurality of images included in a first image study and to automatically determine, by executing one or more rules associated with one or more of the first key image, a user, a type of the first image study, a modality generating the first image study, an anatomy, a location of the modality, and patient demographics, a second key image included in at least one second image study. The system displays the second key image with the first key image to aid a user.

16 Claims, 7 Drawing Sheets

(56) References Cited

U.S. PATENT DOCUMENTS

| | | | |
|---|---|---|---|
| 7,130,457 B2 | 10/2006 | Kaufman et al. | |
| 7,428,323 B2 | 9/2008 | Hillman | |
| 7,529,394 B2 | 5/2009 | Krishnan et al. | |
| 7,640,051 B2 | 12/2009 | Krishnan et al. | |
| 7,672,491 B2 | 3/2010 | Krishnan et al. | |
| 7,761,345 B1 | 7/2010 | Martin et al. | |
| 7,788,040 B2 | 8/2010 | Haskell et al. | |
| 7,949,167 B2 | 5/2011 | Krishnan et al. | |
| 8,021,045 B2 | 9/2011 | Foos et al. | |
| 8,107,700 B2 | 1/2012 | Daw et al. | |
| 8,199,985 B2 | 6/2012 | Jakobsson et al. | |
| 8,340,437 B2* | 12/2012 | Abramoff | G06K 9/6231 382/165 |
| 8,345,940 B2 | 1/2013 | Mattiuzzi et al. | |
| 8,478,698 B1 | 7/2013 | Mah | |
| 8,583,450 B2 | 11/2013 | Baker et al. | |
| 8,687,867 B1 | 4/2014 | Collins et al. | |
| 8,727,989 B2 | 5/2014 | Baba | |
| 8,879,813 B1 | 11/2014 | Solanki et al. | |
| 9,089,303 B2 | 7/2015 | Chen et al. | |
| 9,092,727 B1* | 7/2015 | Reicher | G06F 3/048 |
| 9,245,337 B2 | 1/2016 | Schmidt et al. | |
| 10,127,662 B1* | 11/2018 | Reicher | G06F 16/583 |
| 10,269,114 B2 | 4/2019 | Reicher et al. | |
| 10,275,876 B2 | 4/2019 | Reicher et al. | |
| 10,275,877 B2 | 4/2019 | Reicher et al. | |
| 10,311,566 B2 | 6/2019 | Reicher et al. | |
| 10,332,251 B2 | 6/2019 | Reicher et al. | |
| 2003/0147465 A1* | 8/2003 | Wu | H04N 1/00167 375/240.11 |
| 2004/0147840 A1 | 7/2004 | Duggirala et al. | |
| 2005/0010098 A1 | 1/2005 | Frigstad et al. | |
| 2005/0010445 A1 | 1/2005 | Krishnan et al. | |
| 2005/0021375 A1 | 1/2005 | Shimizu et al. | |
| 2005/0049497 A1* | 3/2005 | Krishnan | G06F 19/321 600/437 |
| 2005/0113960 A1 | 5/2005 | Karau et al. | |
| 2005/0231416 A1 | 10/2005 | Rowe et al. | |
| 2005/0251013 A1 | 11/2005 | Krishnan et al. | |
| 2005/0255434 A1 | 11/2005 | Lok et al. | |
| 2006/0100018 A1 | 5/2006 | Chen et al. | |
| 2006/0159325 A1 | 7/2006 | Zeineh et al. | |
| 2006/0228015 A1 | 10/2006 | Brockway et al. | |
| 2006/0274928 A1 | 12/2006 | Collins et al. | |
| 2007/0036402 A1 | 2/2007 | Cahill et al. | |
| 2007/0047786 A1 | 3/2007 | Aklilu et al. | |
| 2007/0078679 A1 | 4/2007 | Rose | |
| 2007/0118055 A1 | 5/2007 | McCombs | |
| 2007/0118399 A1 | 5/2007 | Avinash et al. | |
| 2007/0272747 A1 | 11/2007 | Woods et al. | |
| 2008/0046286 A1 | 2/2008 | Halsted | |
| 2008/0126982 A1* | 5/2008 | Sadikali | G06F 19/321 715/810 |
| 2008/0163070 A1* | 7/2008 | Mahesh | G06F 19/321 715/745 |
| 2008/0226147 A1 | 9/2008 | Hargrove et al. | |
| 2009/0080731 A1 | 3/2009 | Krishnapuram et al. | |
| 2009/0092300 A1 | 4/2009 | Jerebko et al. | |
| 2009/0274384 A1* | 11/2009 | Jakobovits | G06F 16/51 382/254 |
| 2009/0299977 A1* | 12/2009 | Rosales | G06Q 50/24 |
| 2009/0326989 A1 | 12/2009 | Crucs | |
| 2010/0042422 A1 | 2/2010 | Summers | |
| 2010/0082692 A1* | 4/2010 | Akinyemi | G06K 9/469 707/797 |
| 2010/0121178 A1 | 5/2010 | Krishnan et al. | |
| 2010/0312734 A1 | 12/2010 | Widrow | |
| 2011/0123079 A1 | 5/2011 | Gustafson | |
| 2011/0228995 A1* | 9/2011 | Batman | G06T 19/00 382/128 |
| 2011/0301447 A1 | 12/2011 | Park et al. | |
| 2012/0001853 A1* | 1/2012 | Tanaka | G06F 3/04886 345/168 |
| 2012/0054652 A1 | 3/2012 | Kawagishi et al. | |
| 2012/0088981 A1 | 4/2012 | Liu et al. | |
| 2012/0172700 A1 | 7/2012 | Krishnan et al. | |
| 2012/0189176 A1 | 7/2012 | Giger et al. | |
| 2012/0237109 A1 | 9/2012 | Rajpoot et al. | |
| 2012/0250961 A1* | 10/2012 | Iwasaki | G06F 19/321 382/128 |
| 2012/0283574 A1 | 11/2012 | Park et al. | |
| 2012/0310399 A1 | 12/2012 | Metzger | |
| 2012/0328178 A1 | 12/2012 | Remiszewski et al. | |
| 2013/0090554 A1 | 4/2013 | Zvuloni et al. | |
| 2013/0149682 A1 | 6/2013 | Raab | |
| 2013/0204115 A1 | 8/2013 | Dam et al. | |
| 2013/0290225 A1 | 10/2013 | Kamath et al. | |
| 2013/0304751 A1 | 11/2013 | Yoshioka et al. | |
| 2013/0314434 A1 | 11/2013 | Shetterly et al. | |
| 2014/0010432 A1 | 1/2014 | Cohen-Solal et al. | |
| 2014/0121487 A1 | 5/2014 | Faybishenko et al. | |
| 2014/0155763 A1 | 6/2014 | Bruce | |
| 2014/0161337 A1 | 6/2014 | Raykar et al. | |
| 2014/0185888 A1 | 7/2014 | Kelm et al. | |
| 2014/0218397 A1 | 8/2014 | Rutman et al. | |
| 2014/0218552 A1* | 8/2014 | Huang | G11B 27/034 348/218.1 |
| 2014/0219526 A1 | 8/2014 | Linguraru et al. | |
| 2014/0244309 A1 | 8/2014 | Francois | |
| 2014/0257854 A1 | 9/2014 | Becker et al. | |
| 2014/0279807 A1 | 9/2014 | Dimitrijevic | |
| 2014/0313222 A1 | 10/2014 | Anderson et al. | |
| 2014/0314292 A1 | 10/2014 | Kamen et al. | |
| 2014/0375671 A1 | 12/2014 | Giger et al. | |
| 2015/0065803 A1 | 3/2015 | Douglas et al. | |
| 2015/0072371 A1 | 3/2015 | Marugame | |
| 2015/0091778 A1* | 4/2015 | Day | G06F 3/1446 345/1.3 |
| 2015/0103170 A1 | 4/2015 | Nelson et al. | |
| 2015/0205917 A1 | 7/2015 | Mabotuwana et al. | |
| 2015/0230876 A1 | 8/2015 | Roe et al. | |
| 2015/0235365 A1* | 8/2015 | Mankovich | G06T 7/0014 382/131 |
| 2015/0262014 A1* | 9/2015 | Iwamura | G06K 9/6253 382/128 |
| 2015/0287192 A1 | 10/2015 | Sasaki | |
| 2015/0302317 A1 | 10/2015 | Norouzi et al. | |
| 2015/0320365 A1 | 11/2015 | Schulze et al. | |
| 2015/0325018 A1* | 11/2015 | Ben Ayed | G06T 7/11 382/132 |
| 2015/0331995 A1 | 11/2015 | Zhao et al. | |
| 2015/0332111 A1 | 11/2015 | Kisilev et al. | |
| 2016/0005106 A1 | 1/2016 | Giraldez et al. | |
| 2016/0041733 A1* | 2/2016 | Qian | G06F 19/321 715/771 |
| 2016/0275138 A1 | 9/2016 | Rutenberg et al. | |
| 2016/0283489 A1 | 9/2016 | Uy | |
| 2016/0292155 A1* | 10/2016 | Adriaensens | G06F 19/321 |
| 2016/0350480 A1* | 12/2016 | Gerdeman | G06F 19/321 |
| 2016/0350919 A1* | 12/2016 | Steigauf | G06T 7/0014 |
| 2016/0361025 A1 | 12/2016 | Reicher et al. | |
| 2016/0361121 A1 | 12/2016 | Reicher et al. | |
| 2016/0364526 A1 | 12/2016 | Reicher et al. | |
| 2016/0364527 A1 | 12/2016 | Reicher et al. | |
| 2016/0364528 A1 | 12/2016 | Reicher et al. | |
| 2016/0364539 A1 | 12/2016 | Reicher et al. | |
| 2016/0364630 A1 | 12/2016 | Reicher et al. | |
| 2016/0364631 A1 | 12/2016 | Reicher et al. | |
| 2016/0364857 A1* | 12/2016 | Reicher | G06F 19/00 |
| 2016/0364862 A1 | 12/2016 | Reicher et al. | |
| 2017/0039321 A1* | 2/2017 | Reicher | G06F 16/245 |
| 2017/0091937 A1 | 3/2017 | Barnes et al. | |
| 2017/0169192 A1* | 6/2017 | Sevenster | G06F 17/24 |
| 2017/0262584 A1* | 9/2017 | Gallix | G06F 19/321 |
| 2018/0144421 A1 | 5/2018 | Williams et al. | |
| 2018/0260949 A1* | 9/2018 | Kreeger | G06T 7/0012 |

OTHER PUBLICATIONS

Filed Dec. 13, 2017, U.S. Appl. No. 15/840,744.
Filed Jun. 10, 2016, U.S. Appl. No. 15/179,409, US2016/0364862.
Filed Jun. 10, 2016, U.S. Appl. No. 15/179,434, US2016/0364526.

(56) References Cited

OTHER PUBLICATIONS

Filed Jun. 10, 2016, U.S. Appl. No. 15/179,452, US2016/0364527.
Filed Jun. 10, 2016, U.S. Appl. No. 15/179,465, US2016/0364528.
Filed Jun. 10, 2016, U.S. Appl. No. 15/179,501, US2016/0364630.
Filed Jun. 10, 2016, U.S. Appl. No. 15/179,506, US2016/0364631.
Filed Jun. 10, 2016, U.S. Appl. No. 15/179,674, US2016/0364539.
Filed Jun. 10, 2016, U.S. Appl. No. 15/179,681, US2016/0361025.
Filed Jun. 10, 2016, U.S. Appl. No. 15/179,448, US2016/0364857.
Filed Jun. 10, 2016, U.S. Appl. No. 15/179,457, US2016/0361121.
Chen et al., "An Automatic Diagnostic System for CT Liver Image Classification", IEEE Transactions on Biomedical Engineering, Jun. 6, 1998, pp. 783-794, vol. 45, No. 6.
Goldbaum et al., "Automated Diagnosis and Image Understanding with Object Extraction, Object Classification, and Inferencing in Retinal Images", Department of Ophthalmology and Department of Engineering and Computer Science, 1996, 4 pages, University of California, La Jolla, CA, USA.
Office Action from the US Patent and Trademark Office for U.S. Appl. No. 15/179,501 dated Oct. 10, 2017 (14 pages).
Office Action from the US Patent and Trademark Office for U.S. Appl. No. 15/179,681 dated Oct. 16, 2017 (30 pages).
Piccolo et al., "Dermoscopic diagnosis by a trained clinician vs. a clinician with minimal dermoscopy training vs. computer-aided diagnosis of 341 pigmented skin lesions: a comparative study", Bristish Journal of Dermatology, (2002), vol. 147, pp. 481-486, Bristish Association of Dermatologists.
Binder et al., "Application of an artificial neural network in epiluminescene microscopy pattern analysis of pigmented skin lesions: a pilot study", Bristish Journal of Dermatology, (1994), vol. 130, pp. 460-465.
Carlson et al., "Pancreatic cystic neoplasms: the role and sensitivity of needle aspiration and biopsy", Abdom Imaging, (1998), vol. 23, pp. 387-393, American Roentgen Ray Society, Washington D.C.
Office Action from the US Patent and Trademark Office for U.S. Appl. No. 15/179,465 dated Oct. 13, 2017 (31 pages).
Office Action from the US Patent and Trademark Office for U.S. Appl. No. 15/179,674 dated Oct. 30, 2017 (30 pages).
Scott et al., "Telemedical Diagnosis of Retinopathy of Prematurity: Intraphysician Agreement between Ophthalmoscopic Examination and Image-Based Interpretation", Opthamology, (Jul. 2008), vol. 115, No. 7.
Office Action from the US Patent and Trademark Office for U.S. Appl. No. 15/179,448 dated Oct. 31, 2017 (14 pages).
Office Action from the US Patent and Trademark Office for U.S. Appl. No. 15/179,457 dated Nov. 17, 2017 (15 pages).
Office Action from the U.S. Patent and Trademark Office for U.S. Appl. No. 15/179,506 dated Jan. 11, 2018 (10 pages).
Final Office Action from the U.S. Patent and Trademark Office for U.S. Appl. No. 15/179,465 dated Feb. 28, 2018 (32 pages).
Final Office Action from the U.S. Patent and Trademark Office for U.S. Appl. No. 15/179,681 dated Feb. 28, 2018 (23 pages).
Lavrenko, JJV. et al.; "Automatic Image Annotation and Retrieval Using Cross-Media Relevance Models"; SIGIR'03; Jul. 28-Aug. 1, 2003.
Wang, L. et al.; "Automatic Image Annotation and Retrieval Using Subspace Clustering Algorithm"; MMDB'04; Nov. 13, 2004.
IPCOM000191498D; "Methods and Systems for Medical Image Analysis"; http://ip.com/IPCOM/000191498D; Jan. 6, 2010.
Anonymously; "Method of Providing Translucent Annotations in Medical Images"; http://ip.com/IPCOM/000152706D; May 10, 2007.
Non-Final Office Action from the U.S. Patent and Trademark Office for U.S. Appl. No. 15/179,434 dated Mar. 12, 2018 (12 pages).
Final Office Action from the U.S. Patent Office for U.S. Appl. No. 15/179,501 dated Apr. 9, 2018 (15 pages).
Final Office Action from the U.S. Patent Office for U.S. Appl. No. 15/179,506 dated Jun. 8, 2018 (11 pages).
Final Office Action from the U.S. Patent Office for U.S. Appl. No. 15/179,448 dated May 2, 2018 (15 pages).
Final Office Action from the U.S. Patent Office for U.S. Appl. No. 15/179,457 dated Apr. 30, 2018 (15 pages).
Non-Final Office Action from the U.S. Patent Office for U.S. Appl. No. 15/179,409 dated Jun. 15, 2018 (11 pages).
Notice of Allowance from the U.S. Patent and Trademark Office for U.S. Appl. No. 15/179,465 dated Jul. 25, 2018 (15 pages).
Non-Final Office Action from the U.S. Patent and Trademark Office for U.S. Appl. No. 15/179,674 dated Jul. 11, 2018 (14 pages).
Non-Final Office Action from the U.S. Patent and Trademark Office for U.S. Appl. No. 15/179,681 dated Jul. 9, 2018 (29 pages).
Kim, N. et al., "An Engineering View on Megatrends in Radiology: Digitization to Quantitative Tools of Medicine", Korean Journal of Radiology, Mar.-Apr. 2013, vol. 14, No. 2, pp. 139-153.
Teng. C., "Managing DICOM Image Metadata with Desktop Operating Systems Native User Interface", 22nd IEEE International Symposium on Computer-Based Medical Systems, 2009, (5 pages).
Doi, K., "Computer-aided diagnosis in medical imaging: Historical review, current status and future potential", Computerized Medical Imaging and Graphics, vol. 31, 2007, pp. 198-211.
Final Office Action from the U.S. Patent and Trademark Office for U.S. Appl. No. 15/179,434 dated Oct. 11, 2018 (27 pages).
Non-Final Office Action from the U.S. Patent and Trademark Office for U.S. Appl. No. 15/179,452 dated Oct. 19, 2018 (17 pages).
Notice of Allowance from the U.S. Patent and Trademark Office for U.S. Appl. No. 15/179,681 dated Oct. 30, 2018 (14 pages).
Notice of Allowance from the U.S. Patent and Trademark Office for U.S. Appl. No. 15/179,674 dated Oct. 18, 2018 (8 pages).
Non-Final Office Action from the U.S. Patent and Trademark Office for U.S. Appl. No. 15/179,409 dated Dec. 13, 2018 (47 pages).
Notice of Allowance from the U.S. Patent and Trademark Office for U.S. Appl. No. 15/179,434 dated Dec. 28, 2018 (9 pages).
Corrected Notice of Allowability from the U.S. Patent and Trademark Office for U.S. Appl. No. 15/179,681 dated Jan. 17, 2019 (7 pages).
Notice of Allowance from the U.S. Patent and Trademark Office for U.S. Appl. No. 15/179,448 dated Jan. 23, 2019 (9 pages).
Notice of Allowance from the U.S. Patent and Trademark Office for U.S. Appl. No. 15/179,457 dated Dec. 14, 2018 (8 pages).
Notice of Allowance from the U.S. Patent and Trademark Office for U.S. Appl. No. 15/179,501 dated Feb. 8, 2019 (9 pages).
Corrected Notice of Allowability from the U.S. Patent and Trademark Office for U.S. Appl. No. 15/179,674 dated Jan. 17, 2019 (7 pages).
Supplemental Notice of Allowability from the U.S. Patent and Trademark Office for U.S. Appl. No. 15/179,457 dated Feb. 1, 2019 (8 pages).
Final Office Action from the U.S. Patent and Trademark Office for U.S. Appl. No. 15/179,452 dated Mar. 8, 2019 (13 pages).
Supplemental Notice of Allowability from the U.S. Patent and Trademark Office for U.S. Appl. No. 15/179,448 dated Feb. 27, 2019 (4 pages).
Non-Final Office Action from the U.S. Patent and Trademark Office for U.S. Appl. No. 15/840,744 dated Mar. 5, 2019 (16 pages).
Supplemental Notice of Allowability from the U.S. Patent and Trademark Office for U.S. Appl. No. 15/1,43 dated Feb. 1, 2019 (5 pages).
Notice of Allowance from the U.S. Patent and Trademark Office for U.S. Appl. No. 15/179,506 dated Mar. 12, 2019 (7 pages).
Supplemental Notice of Allowability from the U.S. Patent and Trademark Office for U.S. Appl. No. 15/179,501 dated Mar. 27, 2019 (15 pages).
Corrected Notice of Allowability from the U.S. Patent and Trademark Office for U.S. Appl. No. 15/179,674 dated Mar. 25, 2019 (11 pages).
Corrected Notice of Allowability from the U.S. Patent and Trademark Office for U.S. Appl. No. 15/179,681 dated Mar. 25, 2019 (11 pages).
Supplemental Notice of Allowability from the U.S. Patent and Trademark Office for U.S. Appl. No. 15/179,448 dated Mar. 13, 2019 (7 pages).
Supplemental Notice of Allowability from the U.S. Patent and Trademark Office for U.S. Appl. No. 15/179,457 dated Apr. 1, 2019 (7 pages).
Final Office Action from the U.S. Patent and Trademark Office for U.S. Appl. No. 15/179,409 dated Jun. 13, 2019 (46 pages).

(56) References Cited

OTHER PUBLICATIONS

Applicant-Initiated Interview Summary from the U.S. Patent and Trademark Office for U.S. Appl. No. 15/179,452 dated May 28, 2019 (3 pages).
Applicant-Initiated Interview Summary from the U.S. Patent and Trademark Office for U.S. Appl. No. 15/840,744 dated May 23, 2019 (3 pages).
Examiner Answer to Appeal to Appeal Brief from the U.S. Patent and Trademark Office for U.S. Appl. No. 15/179,409 dated Mar. 5, 2020 (15 pages).
Examiner Answer to Appeal to Appeal Brief from the U.S. Patent and Trademark Office for U.S. Appl. No. 15/840,744 dated May 15, 2020 (14 pages).
Supplemental Notice of Allowability from the U.S. Patent and Trademark Office for U.S. Appl. No. 15/179,448 dated Apr. 1, 2019 (7 pages).
Advisory Action from the U.S. Patent and Trademark Office for U.S. Appl. No. 15/179,452 dated May 28, 2019 (3 pages).
Advisory Action from the U.S. Patent and Trademark Office for U.S. Appl. No. 15/840,744 dated Oct. 11, 2019 (3 pages).

* cited by examiner

AUTOMATED SELECTION, ARRANGEMENT, AND PROCESSING OF KEY IMAGES

FIELD

Embodiments described herein relate to systems and methods for performing image analytics to automatically select, arrange, and process key images as part of a medical image study.

SUMMARY

When physicians, such as radiologists and cardiologists, review medical images captured as part of a clinical imaging procedure for the purpose of creating a clinical report, they commonly select key images. "Key images," as this term is used in the medical industry, identify "important" images in a study. Key images may be displayed in a montage, such as a single composite image or as individual images separately displayed, such as in a virtual stack of images. The key images may include images supporting a normal finding, an abnormality, a change from previous image studies, or the like. In some embodiments, to provide a proper diagnosis, a reviewing physician compares one or more of these key images to one or more images included in another image study, sometimes referred to as a "comparison image study." Accordingly, the reviewing physician must be able to located relevant comparison image studies and properly compare images between multiple studies or risk providing a misdiagnosis.

Thus, embodiments described herein improve clinical efficiency and accuracy related to reading and reporting medical images using rules and, in some embodiments, artificial intelligence. In particular, embodiments described herein assist reading physicians in selecting, arranging, processing, and reporting key images from a current image study and comparison image studies using automated, rules-based actions to expedite the reading and reporting of medical images.

For example, in one embodiment, the invention provides a system for automatically determining a key image for display to a user and/or storage as part of analyzing an image study generated as part of a medical imaging procedure. The system includes a memory storing a plurality of image studies, each of the plurality of image studies including a plurality of images; a display device for displaying images; and an electronic processor interacting with the memory and the display device. The electronic processor is configured to: determine a first key image within a plurality of images included in a first image study; automatically determine, by executing one or more rules associated with one or more of the first key image, a user, a type of the first image study, a modality generating the first image study, an anatomy, a location of the modality, and patient demographics, at least one second key image included in at least one second image study included in the plurality of image studies stored in the memory; and display, via the display device, the second key image with the first key image to aid a user in study of the first image study.

Another embodiment provides a method of automatically determining a key image for display to a user and/or for storage as part of analyzing an image study generated as part of a medical imaging procedure. The method includes: determining a first key image within a plurality of images included in a first image study; automatically determining, with an electronic processor, by executing one or more rules associated with one or more of the first key image, a user, a type of the first image study, a modality generating the first image study, an anatomy, a location of the modality, and patient demographics, at least one second key image included in at least one second image study included in a plurality of image studies stored in a memory; and displaying, with the electronic processor via a display device, the second key image with the first key image within a montage template to aid a user in study of the first image study.

Another embodiment is directed to a non-transitory computer medium including instructions that, when executed as a set of instructions by an electronic processor perform a set of operations. The operations determine a first key image within a plurality of images included in a first image study; automatically determine, by executing one or more rules associated with one or more of the first key image, a user, a type of the first image study, a modality generating the first image study, an anatomy, a location of the modality, and patient demographics, at least one second key image included in at least one second image study included in a plurality of image studies stored in a memory, the one or more rules generated using machine learning; and display, via a display device, the second key image with the first key image to aid a user in study of the first image study.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or couplings, whether direct or indirect. Also, electronic communications and notifications may be performed using any known means including direct connections, wireless connections, etc.

A plurality of hardware and software based devices, as well as a plurality of different structural components may be utilized to implement the invention. In addition, embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the invention may be implemented in software (e.g., stored on non-transitory computer-readable medium) executable by one or more processors. As such, it should be noted that a plurality of hardware and software based devices, as well as a plurality of different structural components, may be utilized to implement the invention. For example, "mobile device," "computing device," and "server" as described in the specification may include one or more electronic processors, one or more memory modules including non-transitory computer-readable medium, one or more input/output interfaces, and various connections (e.g., a system bus) connecting the components.

Figure 1:
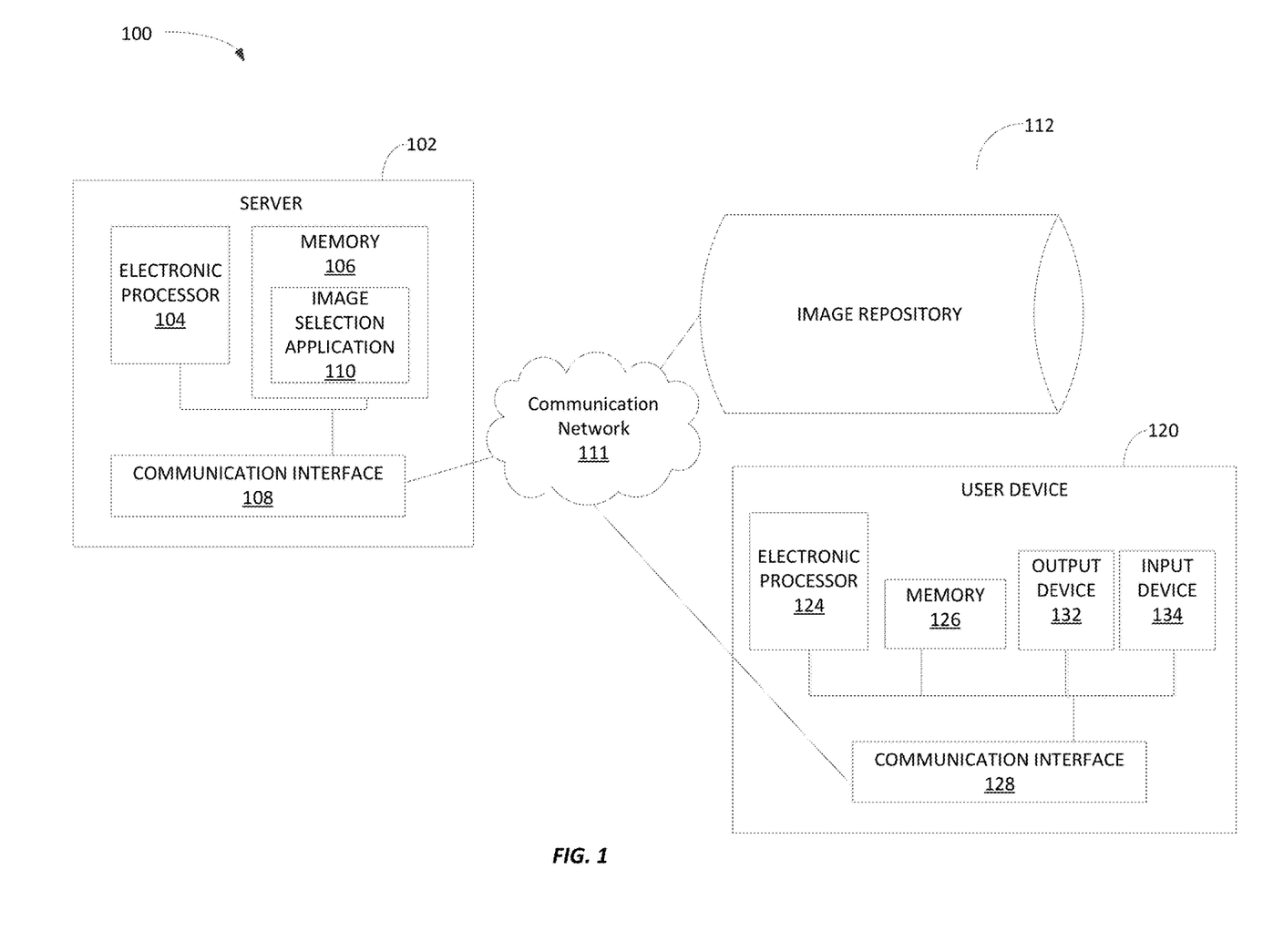
FIG. 1 illustrates a system for performing image analytics according to one embodiment.

FIG. 1 illustrates a system 100 for automatically selecting, arranging, and processing images. The system 100 includes a server 102 that includes a plurality of electrical and electronic components that provide power, operational control, and protection of the components within the server 102. For example, as illustrated in FIG. 1, the server 102 may include an electronic processor 104 (e.g., a microprocessor, application-specific integrated circuit (ASIC), or another suitable electronic device), a memory 106 (e.g., a non-transitory, computer-readable storage medium), and a communication interface 108. The electronic processor 104, the memory 106, and the communication interface 108 communicate over one or more connections or buses. The server 102 illustrated in FIG. 1 represents one example of a server and embodiments described herein may include a server with additional, fewer, or different components than the server 102 illustrated in FIG. 1. Also, in some embodiments, the server 102 performs functionality in addition to the functionality described herein. Similarly, the functionality performed by the server 102 (i.e., through execution of instructions by the electronic processor 104) may be distributed among multiple servers. Accordingly, functionality described herein as being performed by the electronic processor 104 may be performed by one or more electronic processors included in the server 102, external to the server 102, or a combination thereof.

The memory 106 may include read-only memory ("ROM"), random access memory ("RAM") (e.g., dynamic RAM ("DRAM"), synchronous DRAM ("SDRAM"), and the like), electrically erasable programmable read-only memory ("EEPROM"), flash memory, a hard disk, a secure digital ("SD") card, other suitable memory devices, or a combination thereof. The electronic processor 104 executes computer-readable instructions ("software") stored in the memory 106. The software may include firmware, one or more applications, program data, filters, rules, one or more program modules, and other executable instructions. For example, as illustrated in FIG. 1, in some embodiments, the memory 106 stores an image selection application 110. As described in more detail below, the image selection application 110 is configured to apply rules to automatically select, arrange, and process key images for an image study.

It should be understood that the functionality described herein as being performed by the image selection application 110 may be distributed among multiple modules or applications (executed by the server 102 or multiple servers or devices). Also, in some embodiments, the functionality described herein as being performed by the image selection application 110 (or portions there) are performed by one or more software applications executed by other computing devices, such as the user device 120 described below. The memory 106 may also store rules applied by the image selection application 110 as described herein. However, in other embodiments, the rules may be stored separate from the application 110.

The communication interface 108 allows the server 102 to communicate with devices external to the server 102. For example, as illustrated in FIG. 1, the server 102 may interact or communicate with one or more image repositories 112 through the communication interface 108. In particular, the communication interface 108 may include a port for receiving a wired connection to an external device (e.g., a universal serial bus ("USB") cable and the like), a transceiver for establishing a wireless connection to an external device over one or more communication networks 111 (e.g., the Internet, a local area network ("LAN"), a wide area network ("WAN"), and the like), or a combination thereof.

In some embodiments, the server 102 acts as a gateway to the one or more image repositories 112. For example, in some embodiments, the server 102 may be picture archiving and communication system ("PACS") server that communicates with one or more image repositories 112. However, in other embodiments, the server 102 may be separate from a PACS server and may communicate with a PACS server to access images stored in one or more image repositories.

As illustrated in FIG. 1, the server 102 also communicates with a user device 120 (e.g., a personal computing device, such as but not limited to a laptop computer, a desktop computer, a terminal, a tablet computer, smart phone, a smart watch or other wearable, a smart television, and the like). The user device 120 may communicate with the server 102 via the communication network 111. The user device 120 may communicate with the server 102 to access one or more images stored in the one or more image repositories 112. For example, a user may use a browser application executed by the user device 120 to access a web page provided by the server 102 for accessing (viewing) one or more images. In other embodiments, the user may use a dedicated application executed by the user device 120 (a viewer application) to retrieve images from the image repositories 112 via the server 102.

As illustrated in FIG. 1, the user device 120 includes similar components as the server 102, such as an electronic processor 124, a memory 126, and a communication interface 128 for communicating with external devices, such as via the communication network 111. The user device 120 also includes at least one output device 132, such as one more display devices, one or more speakers, and the like configured to provide output to a user, and at least one input device 134, such as a microphone, a keyboard, a cursor-control, device, a touchscreen, or the like configured to receive input from a user.

Figure 2:
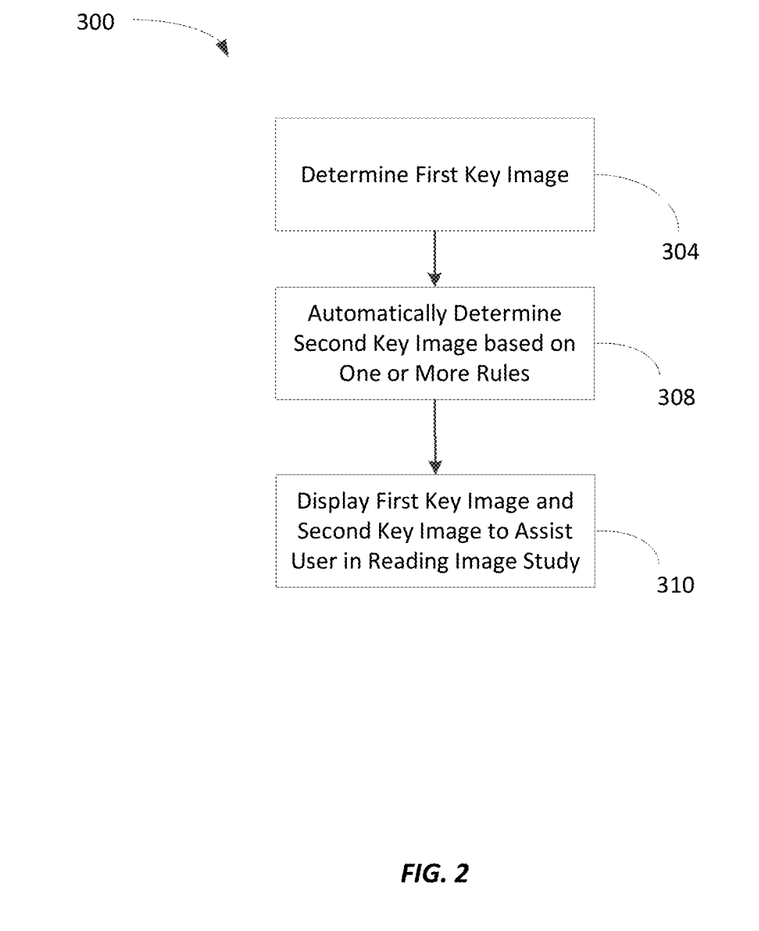
FIG. 2 is flowchart of a method performed by the system of FIG. 1 for automatically selecting a key image for an image study according to one embodiment.

FIG. 2 is a flowchart illustrating a method 300 performed by the server 102 (i.e., the electronic processor 104 executing instructions, such as the image selection application 110) for automatically selecting, arranging, and processing medical images according to some embodiments. As noted above, in some embodiments, the user device 120 may be configured to execute one or more software applications to perform all or a portion of the functionality described herein as being performed via execution of the image selection application 110.

Figure 3:
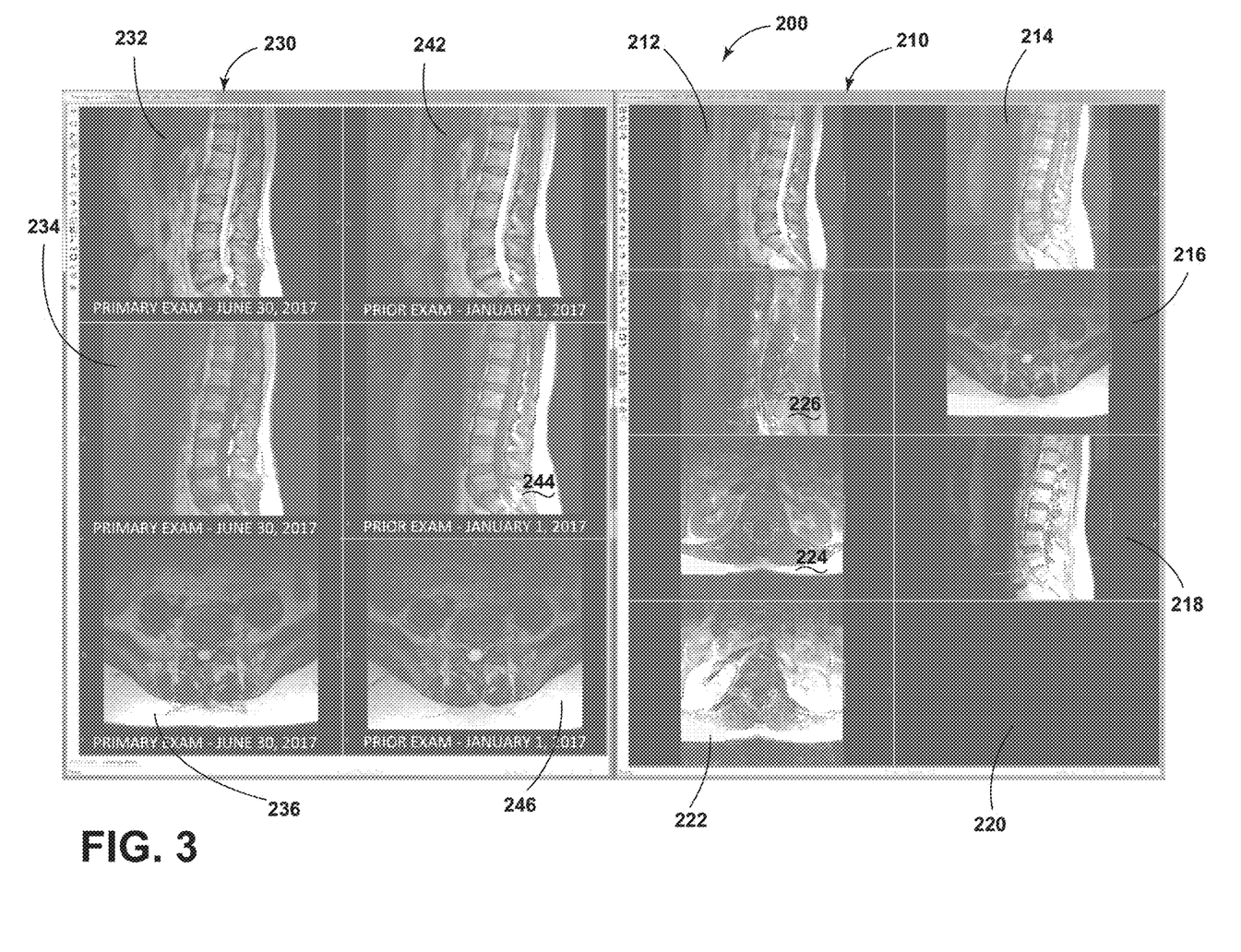
FIGS. 3-4 and 6 illustrate graphical user interfaces for selecting and displaying key images for an image study according to various embodiments.

In some embodiments, the image selection application 110 performs the functionality described herein in response to various triggering events. For example, in some embodiments, the image selection application 110 perform the functionality described herein in response to a reviewing or reading physician accessing or viewing a particular image study. For example, FIG. 3 shows a graphical user interface ("GUI") 200 provided on a display device of the user device 120. In FIG. 3, the right tab 210 or right panel shows various images 212, 214, 216, 218, 220, 222, 224, 226 from an image study available for manual selection by the user. The left tab 230 or left panel provided on the graphical user interface 200 includes a column or vertically oriented row of medical images 232, 234, 236 from a primary or current image study, along with a column or vertically oriented row of images 242, 244, 246 from a previous or prior image study that form a collection of images provided in a montage. In some embodiments, the primary or current image study includes the most recent medical imaging procedure conducted on a particular patient or an image study needing a diagnosis.

Returning to FIG. 2, the electronic processor 104 is configured to determine a first key image (at block 304). In one embodiment, the electronic processor 104 is configured to determine the first key image based on input received from a user selecting a particular image as a key image. For example, using the example GUI 200 illustrated in FIG. 3, a user may manually select a key image by selecting one of the images 212, 214, 216, 218, 220, 222, 224 and moving the image, or an enlarged portion of the image, to the location of the image 232 in the left tab 230. Thus, a user manually selects the first key image and positions the first key image within the montage on the left tab 230. The user may manually select the first key image via a mouse click, an audio command via a microphone, a keyboard shortcut, a touchscreen action, or dragging or swiping an image. In other embodiments, the electronic processor 104 is configured to automatically determine the first key image. For example, the electronic processor 104 may be configured to automatically identify particular anatomy in an image, abnormalities in an image, normal findings in an image, or the like and, thus, may be configured to automatically select an image as a key image. In some embodiments, the electronic processor 104 may be configured to automatically select key images using the image analytics as described in U.S. patent application Ser. Nos. 15/179,506 and 15/179,465, both filed Jun. 10, 2016. The entire content of each of these applications is incorporated by reference herein. Accordingly, it should be understood that, as used in the present application, a "key image" includes an image (or a portion thereof) (i) manually identified as a key image or (ii) automatically determined as a key image using various image analytics techniques and methodologies.

As one example, an image included in a current image study may include an index lesion, defined as a key finding that is representative of the patient's problem or shows a pertinent negative finding. Such an index lesion could be identified because of an action of the reading physician or automatically because the anatomical position matches the location of a previously marked index lesion in the same patient. Under any one of these circumstances, when the image is added to the montage (meaning marked as a key image and/or added to a specific montage of images), the electronic processor 104 is configured to automatically select another key image (e.g., the best matching comparison image that also contains the same index lesion) as described below.

In particular, regardless of whether the first key image was determined from input from a user or automatically, the electronic processor 104 is configured to automatically determine a second image based on one or more rules (at block 308). The rules may consider characteristics of the first key image, the exam type, the modality type, patient demographics, user findings, or the like. For example, the rules may specify that when the first key image is selected from a magnetic resonance ("MR") image ("MRI") study and the initial diagnosis (provided by the user or automatically using image analytics) is "normal," a predetermined set of images (of particular anatomy, with particular image characteristics or positions, or the like) should be automatically included in the set of key images. The rules may use metadata for an image or image study (e.g., DICOM header data), patient data, clinical data, and the like to automatically select the second key image.

It should be understood that the second key image may be included in the same image study as the first key image or a different image study. In particular, in some embodiments, the second key image is included in a prior comparison image study. In this situation, the second key image may include a key image or nonkey image from a comparison image study. However, in other embodiments, the second key image may be an image within the comparison study identified by the electronic processor 104 (regardless of whether the image was identified as a key image in the comparison image study) as being relevant, such as by analyzing and interpreting a diagnosis or finding (as recorded in a structured report for the comparison image study) for the comparison image study or by anatomically matching to a location of a key image in the current study. It should be understood that, in some embodiments, the first key image may be included in the comparison image study and the second key image may also be included in the comparison image study, another comparison image study, or a current image study being reviewed by a user.

The rules may be customized for individual users or groups of users, such as by user, user role, a location of the modality generating the image study, the location of the user, a modality, an exam type, a body part associated with the image study or a particular image, patient demographics, a network of the user, a clinic the user is associated with, a referring physician, and the like. Thus, for example, if a particular physician selects a key image, the electronic processor 104 may be configured to automatically select and apply a rule for the modality and finding that is specific to the user as compared to other rules for the same modality and finding.

As illustrated in FIG. 2, the electronic processor 104 displays the first key image and the second key image to aid a user in studying and reading the first image study (at block 310). In some embodiments, the second key image and the first key image are displayed in a montage template, such as a montage displayed on the left tab 230 in FIG. 3. For example, as illustrated in FIG. 3, the image 232 is a first key image selected by a user, and the image 242 is a previous image determined by the electronic processor 104 to be the second key image. As also illustrated in FIG. 3, the image 232 may be displayed adjacent the first key image 232 for comparison purposes. In some embodiments, the rules used to automatically select the second key image may also specify (based on a template provided for the montage, a position of the first key image, or a combination thereof)

where to position the second key image within the montage. As noted above, these portions of the rules may be customized based on preferences of a user, a group of users, or the like.

In some embodiments, the electronic processor 104 is also configured to automatically generate text or labels for the key images. For example, FIG. 3 illustrates descriptive text for an image, such as the date of the image study including the key image (e.g., "Jun. 30, 2017").

In some embodiments, the electronic processor 104 is also configured to automatically generate text for a report (a structured report) associated with an image study based on the selection of key images. For example, the electronic processor 104 may be configured to automatically generate text based on what images were compared, what anatomy was reviewed, measurements in images, or the like. This text can be displayed to a user for review, editing (as needed), and approval. In some embodiments, the user may indicate (by selecting a button or other selection mechanism or issuing an audio or verbal command) when all of the key images have been selected (and annotated as needed), which may trigger the electronic processor 104 to generate text for the report.

It should be understood that, in some embodiments, the electronic processor 104 is configured to automatically select multiple key images for an image study (e.g., a third key image, fourth key image, and the like). Each automatically-determined key image may be selected from the same image study, different image studies, or a combination thereof. For example, in some situations, the selected key images may be from different types of image studies or different image studies generated at different times (e.g., to show a treatment progression or change). Further, additional key images, such as images 234, 236 are selectable by a user in a similar manner as discussed above to select additional key images. All of the key images selected for a particular image study are provided as an initial montage, which a user can review, edit, and approve. In particular, the user may have the option to remove or replace key images by selecting and deleting the images.

In some embodiments, the rules described above, are predefined for one or multiple users. The rules may also be manually configurable or changeable by particular users. Alternatively or in addition, the rules may be initially created or modified using machine learning. Machine learning generally refers to the ability of a computer program to learn without being explicitly programmed. In some embodiments, a computer program (e.g., a learning engine) is configured to construct a model (e.g., one or more algorithms) based on example inputs. Supervised learning involves presenting a computer program with example inputs and their desired (e.g., actual) outputs. The computer program is configured to learn a general rule (e.g., a model) that maps the inputs to the outputs. The computer program may be configured to perform deep machine learning using various types of methods and mechanisms. For example, the computer program may perform deep machine learning using decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using all of these approaches, a computer program may ingest, parse, and understand data and progressively refine models for data analytics.

Accordingly, a learning engine (executed by the server 102 or a separate computing device) may be configured to receive example inputs and outputs ("training information") that allows the learning engine to automatically determine the rules described above. In some embodiments, the training information includes information regarding what images were selected as key images for previously-reviewed image study, what images were annotated, a diagnosis for the image study or individual images, or the like. Again, machine learning techniques as described in U.S. patent application Ser. Nos. 15/179,506 and 15/179,465 (incorporated by reference herein) may be used to automatically create or modify the rules described herein for automatically selecting key images. User interaction with selected key images may also be used as feedback to such a learning engine to further refine the rules. For example, when a particular user repeatedly adds a particular image to a montage, deletes an automatically-selected image from a montage, changes the position of an image in the montage, or a combination thereof, the learning engine may be configured to detect a pattern in such manual behavior and modify the rules (such as user-specific rules) accordingly.

Figure 4:
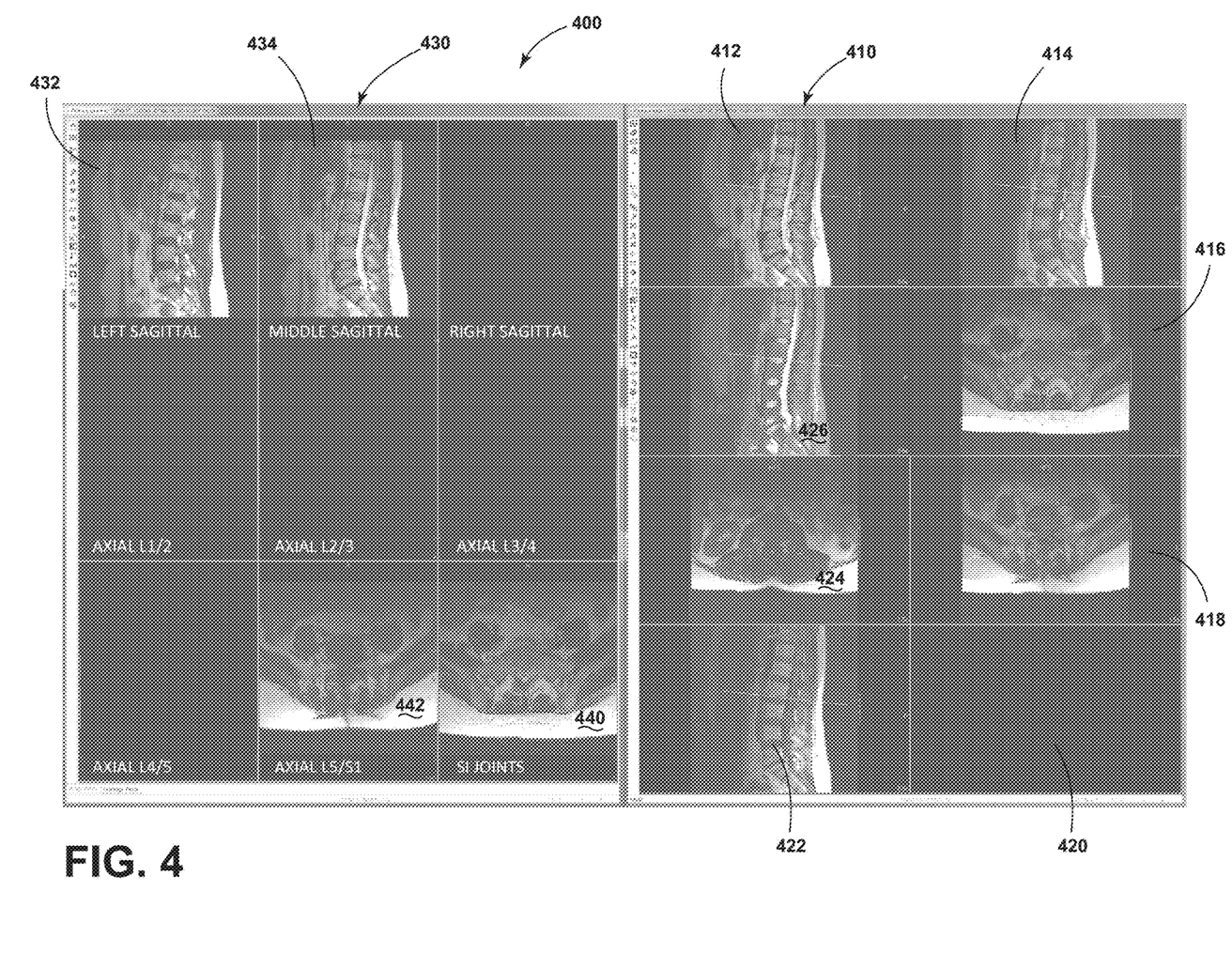

As noted above, in addition to selecting key images, a user may also position key images within a montage (e.g., at particular positions). For example, FIG. 4 shows a graphical user interface ("GUI") 400 provided on a display device. The right tab 410 or right panel shows various 412, 414, 416, 418, 420, 422, 424, 426 from an image study, and the left tab or left panel is a montage template 430 includes three rows and three columns of partially filled spaces for medical images, some of which include medical images 432, 434, 440, 442 for a back and lumbar regions of a patient. The images 432, 434, 440, 442 have been selected as key images in the example illustrated in FIG. 4. As discussed above, in some embodiments, one or more of the images 432, 434, 440, 442 are manually dragged into the montage template 430. Alternatively or in addition, one or more of the images 432, 434, 440, 442 are automatically selected and positioned within the montage template 430. Based on an images position within the montage template, the electronic processor 104 may be configured to automatically generate a label for an image within the template 430.

Figure 5:
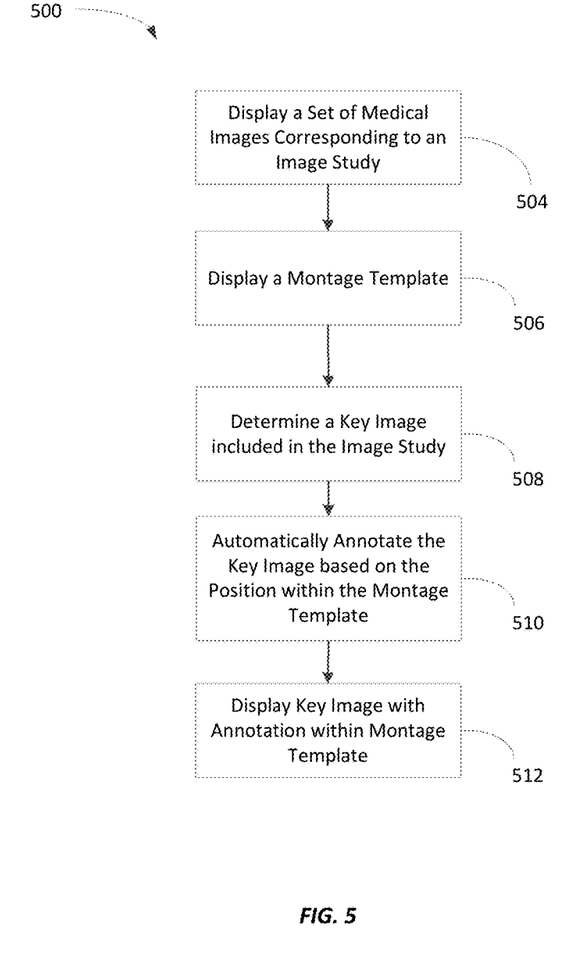
FIG. 5 is a flowchart of a method performed by the system of FIG. 1 for automatically annotating key images for an image study according to one embodiment.

For example, FIG. 5 is a flow chart illustrating a method 500 for automatically labeling an image included in a montage. The method 500 is described as being performed by the server 102 (e.g., through execution of instructions, such as the image selection application 110, by the electronic processor 104). However, as noted above, in some embodiments, the user device 120 may be configured to perform all or a subset of the functionality illustrated in FIG. 5.

Figure 6:
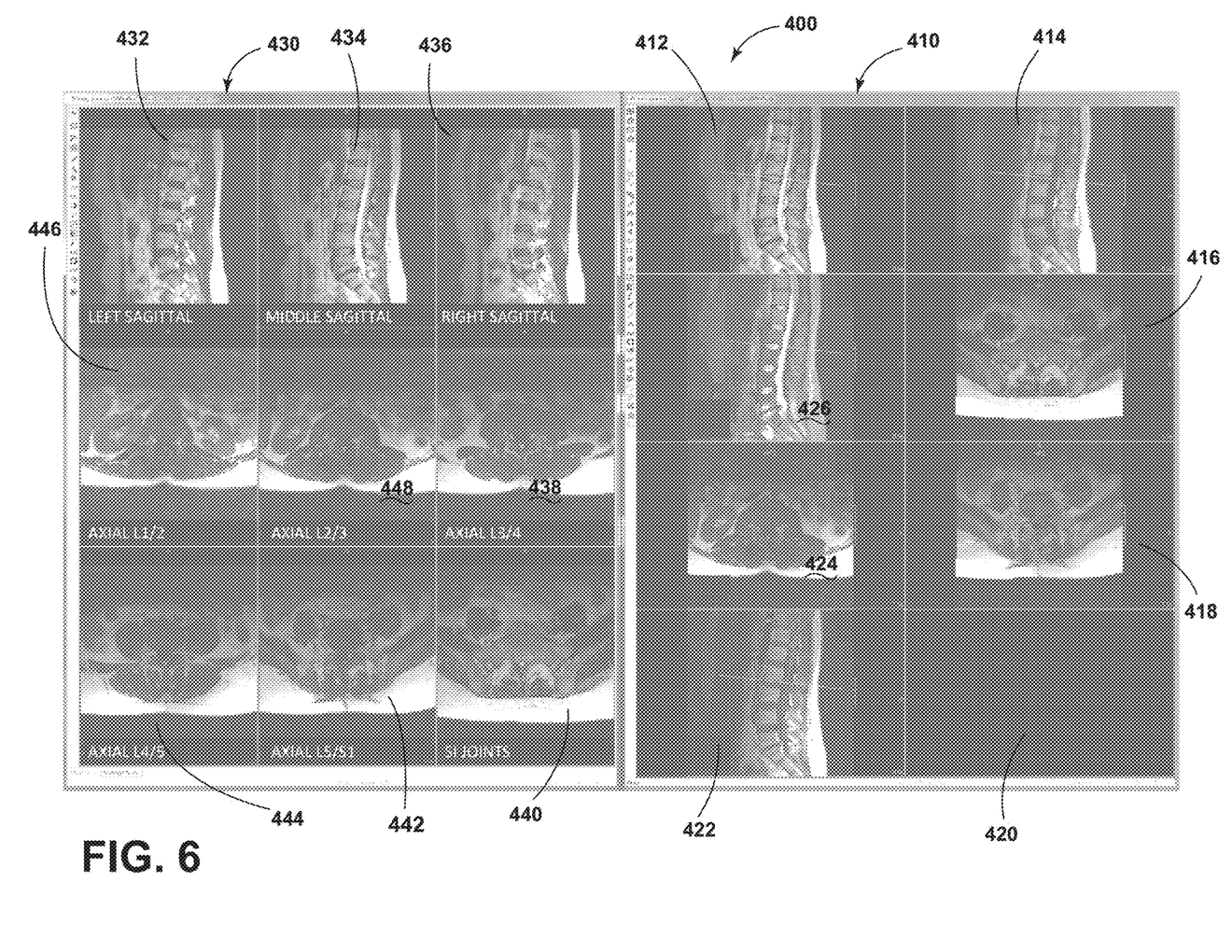
Figure 7:
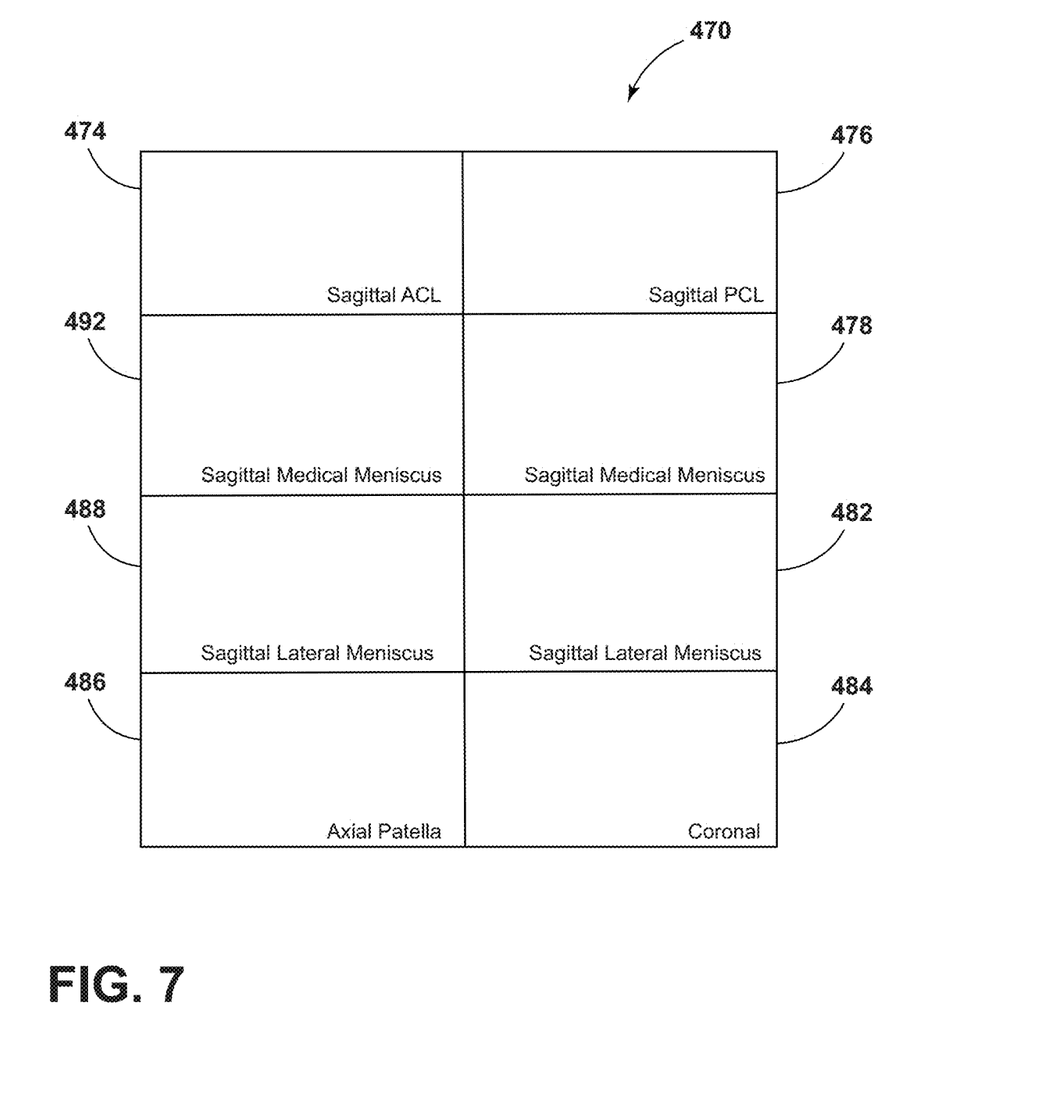
FIG. 7 is a block diagram illustrating a montage template including a plurality of sub-containers.

The functionality of FIG. 5 is described, as one example, with respect to FIGS. 6 and 7. FIG. 6 shows the montage template 430 completed with medical images 432, 434, 436, 438, 440, 442, 444, 446, 448 provided in display sub-containers on a display device for multiple components of the back of the patient. In one embodiment, the right tab 410 is a first tab, and the left tab defining the montage template 430 is a second tab. FIG. 7 schematically illustrates the configuration of a montage template 470 for a MRI of a knee of a patient. The montage template 470 may be disposed in, for instance, the left tab shown in FIG. 6 in one embodiment.

As illustrated in FIG. 5, the electronic processor 104 is configured to display a set of medical images corresponding to an image study on the at least one display device (at block 504 in FIG. 5) as shown by the images in the right tab 410 in FIG. 6. The electronic processor 104 is also configured to display a montage template (at block 506 in FIG. 5) as shown by the montage templates 430 and 470 as illustrated in FIGS. 6 and 7. In some embodiments, the electronic processor 104 is configured to automatically select the montage template, such as based on a type of the image study (a modality type, procedure type, or the like), patient demographics, an anatomy, key images selected for the image study, user preferences, and the like.

The electronic processor 104 is also configured to determine a key image included in the image study (at block 508). As described above, key images may be determined manually, automatically, or a combination thereof. As also described above, each key image may be positioned within the montage template and, again, this positioning may be performed manually or automatically by the electronic processor 104. Based on the position of the key image within the montage template, the electronic processor 104 is configured to automatically annotate the key image (at block 510) and display the key image with the annotation within the montage template (at block 512). For example, each montage template may include one or more pre-labeled sub-containers that specify required or recommended images. For example, as illustrated in FIG. 7, a montage template for a lumbar spine MRI may include a sagittal ACL sub-container 474, a sagittal PCL sub-container 476, a sagittal medial meniscus sub-container 478, a sagittal lateral meniscus sub-container 482, a coronal sub-container 484, an axial patella sub-container 486, a sagittal lateral meniscus sub-container 488, and a sagittal medial meniscus 492 sub-container. Thus, by positioning the appropriate images from an image study into the appropriate montage position, the electronic processor 104 is configured to automatically label each image (anatomy, positions), which eliminates the need for manual labeling, which can create delay and can introduce human errors.

In addition to labeling key images, one or more sub-containers within a montage template may be associated with particular automated functionality. For example, in some embodiments, the electronic processor 104 is also configured to automatically label other images in an image study based on the labels automatically added to key images positioned within a montage template (e.g., based on an image's position in a series of images with respect to a key image). Similarly, in some embodiments, when a key image is added to a particular sub-container of a montage template, the electronic processor 104 may be configured to automatically select another key image that includes a corresponding image from a comparison image study. The electronic processor 104 may also be configured automatically analyze an image or multiple images to perform various types of analyses. For example, the electronic processor 104 may be configured to compare and describe index lesions, identify anomalies, compare findings or anatomical locations, determine progressions, take measurements, add one or more graphical annotations ("marktations") to an image, or the like. For example, an image from a brain MM showing an index nodular metastasis in the left occipital lobe may be added to a montage and the electronic processor 104 may be configured to automatically compare and describe index lesions, automatically add a brain MM image from the most recent comparison image study, and analyze and reports the progression or regression of the lesion.

The results of such analysis may be provided as text (e.g., for inclusion in a structured report), a table, or the like. For example, the electronic processor 104 may be configured to generate text based on the analysis and display the text to a user for review, editing, and approval. Similarly, the electronic processor 104 may be configured to create a table of findings and analyze the table to determine disease changes, such as by comparing images using one or standard methodologies, such as RECIST 1.1 rules. Such analysis may be reported to the user and, optionally, added to a structured report.

Particular sub-containers may also be designated as required or optional, and the electronic processor 104 may be configured to automatically prompt a user for a key image for such sub-containers and may be configured to prevent the user from submitting or saving a report or finding for an image study until all required key images have been added to the montage.

Different processing may be associated with different sub-containers of a montage template and may also differ depending on the key image positioned within a particular sub-container (or key images positioned in other sub-containers of the montage template). Also, in some embodiments, a user (via the GUI) may be configured to provide a tool that allows the user to associate particular sub-containers with particular functionality. Also, the processing functionalities may be configured to be customized for particular users or groups of users. Furthermore, in some embodiments, the processing for one or more sub-containers may be based on findings or other input from a user and, thus, may be dynamically updated based on user interaction.

Alternatively or in addition, the processing functionality associated with particular montage template may be automatically generated or modified using artificial intelligence as described above for the rules for selecting key images. For example, a learning engine may be configured to automatically learn data patterns associated with labels or actions taken by a user to define processing for a particular sub-container. In some embodiments, a learning engine may also be configured to consider processing performed when a previous exam was read, such as a comparison image study. For example, under the appropriate circumstances, when an image is added to a montage, the electronic processor 104 may attempt to segment and measure the volume of anomalies if this was the processing performed when the comparison exam was read and reported. As an example, when a chest computed tomography ("CT") slice is moved to the montage template, the electronic processor 104 may be configured to detect aortic abnormalities or other specific abnormalities that were assessed on the prior image study or clinical report. Also, feedback from a user regarding automatically-generated text could be provided as part of a closed feedback loop to help the system 100 learn the proper behaviors for processing key images. The labels associated a montage template may also be used automatically learn anatomy based on user actions. For example, labeled images may be used as training data for a learning engine.

In one embodiment, the system analyzes the exam images to understand the anatomical location, such that when a user selects an exam image as a key image, the image is automatically positioned in the proper location in the montage template. Thus, the montage template or key image template can work in two ways in increase efficiency as the template can provide 1) a means for labeling images as to anatomy or other characteristic(s), or 2) a standardized format for key images that specifies an order or location that is automatically filled as key images are selected (as the system can automatically derive these characteristics), or both. The montage template therefore can enhance user consistency and efficiency in multiple ways. In other embodiments, the selection of key images by the user is provided by various automated and semi-automated arrangements. In one embodiment a user clicks on an image. In another embodiment, a user provides an audio command to a conversational audio interface. The system may infer a selection, so that if a user says, "Normal brain", the system might use configured or machine-learned rules to select one or more key images based on inferred actions.

Thus, embodiments described herein provide, among other things, methods and systems for automatically selecting, arranging, and processing key images for a medical image study. As described above, various rules may be applied by the systems and methods to quickly and effectively process image studies that may include hundreds or thousands of images without requiring or minimizing user input or interaction. Machine learning techniques may be used to establish or modify such rules, which further improve the efficiency and effectiveness of the systems and methods. Various features and advantages of the invention are set forth in the following claims.

What is claimed is:

1. A system for automatically determining a key image for display to a user as part of analyzing an image study generated as part of a medical imaging procedure, the system comprising:
a memory storing a plurality of image studies, each of the plurality of image studies including a plurality of images;
a display device for displaying images; and
an electronic processor interacting with the memory and the display device, the electronic processor configured to:
automatically determine a first key image within a plurality of images included in a first image study,
automatically determine, by executing one or more rules associated with one or more of the first key image, a user, a type of the first image study, a modality generating the first image study, an anatomy, a location of the modality, and patient demographics, at least one second key image included in at least one second image study included in the plurality of image studies stored in the memory,
automatically label the first key image from the first image study based on a positon of the first key image within a montage template,
automatically label the second key image from the second image study based on a position of the second key image within the montage template, and
display, via the display device, the second key image with the first key image to aid a user in study of the first image study,
wherein the rules are generated, at least in part, using machine learning.

2. The system of claim 1, wherein the first key image and the second key image are displayed within the montage template.

3. The system of claim 2, wherein the electronic processor is further configured to automatically position the first key image and the second key image within the montage template.

4. The system of claim 1, wherein the second image study is a comparison image study for the first image study.

5. The system of claim 1, wherein the second image study includes a key image previously-selected for the second image study.

6. A method of automatically determining a key image for display to a user as part of analyzing an image study generated as part of a medical imaging procedure, the method comprising:
automatically determining, with an electronic processor, a first key image within a plurality of images included in a first image study;
automatically determining, with the electronic processor, by executing one or more rules associated with one or more of the first key image, a user, a type of the first image study, a modality generating the first image study, an anatomy, a location of the modality, and patient demographics, at least one second key image included in at least one second image study included in a plurality of image studies stored in a memory;
automatically labeling with the electronic processor, the first key image from the first image study based on a position of the first key image within a montage template,
automatically labeling with the electronic processor, the second key image from the second image study based on a position of the second key image within the montage template, and
displaying, with the electronic processor via a display device, the second key image with the first key image within the montage template to aid a user in study of the first image study,
wherein the rules are generated, at least in part, using machine learning.

7. The method of claim 6, further comprising automatically positioning the first key image and the second key image within the montage template.

8. A non-transitory computer medium including instructions that, when executed as a set of instructions by an electronic processor perform a set of operations comprising:
automatically determine, with the electronic processor, a first key image within a plurality of images included in a first image study;
automatically determine, with the electronic processor, by executing one or more rules associated with one or more of the first key image, a user, a type of the first image study, a modality generating the first image study, an anatomy, a location of the modality, and patient demographics, at least one second key image included in at least one second image study included in a plurality of image studies stored in a memory, the one or more rules generated, at least in part, using machine learning;
automatically label the first key image from the first image study based on a position of the first key image within a montage template,
automatically label the second key image from the second image study based on a position of the second key image within the montage template, and
displaying, via a display device, the second key image with the first key image to aid a user in study of the first image study.

9. The method of claim 6, wherein the second image study is a comparison study for the first image study.

10. The method of claim 6, including automatically positioning, with the electronic processor, the first key image and the second key image within the montage template.

11. The method of claim 6, wherein the second image study is a comparison image study for the first image study.

12. The method of claim 6, wherein the second image study includes a key image previously-selected for the second image study.

13. The non-transitory computer medium of claim 8, wherein the first key image and the second key image are displayed within the montage template.

14. The non-transitory computer medium of claim 8, wherein the electronic processor is further configured to automatically position the first key image and the second key image within the montage template.

15. The non-transitory computer medium of claim 8, wherein the second image study is a comparison image study for the first image study.

16. The non-transitory computer medium of claim 8, wherein the second image study includes a key image previously-selected for the second image study.

* * * * *